US012585034B2

(12) United States Patent　　(10) Patent No.:　US 12,585,034 B2
Wu　　(45) Date of Patent:　Mar. 24, 2026

(54) ELECTRONIC DEVICE COMPRISING A FILTER, A SCINTILLATOR, A SENSOR, AND A SUBSTRATE

(71) Applicant: InnoCare Optoelectronics Corporation, Tainan City (TW)

(72) Inventor: Chih-Hao Wu, Tainan City (TW)

(73) Assignee: InnoCare Optoelectronics Corporation, Tainan City (TW)

( * ) Notice: Subject to any disclaimer, the term of this patent is extended or adjusted under 35 U.S.C. 154(b) by 206 days.

(21) Appl. No.: 18/402,665

(22) Filed: Jan. 2, 2024

(65) Prior Publication Data

US 2024/0272313 A1　　Aug. 15, 2024

Related U.S. Application Data

(60) Provisional application No. 63/445,717, filed on Feb. 15, 2023.

(30) Foreign Application Priority Data

Sep. 27, 2023　(TW) ................................. 112137049

(51) Int. Cl.
　　*A61B 6/42*　　　(2024.01)
　　*A61B 6/00*　　　(2006.01)
　　*G01T 1/20*　　　(2006.01)
　　*G01T 1/208*　　　(2006.01)
(52) U.S. Cl.
　　CPC ........ *G01T 1/20187* (2020.05); *A61B 6/4241* (2013.01); *A61B 6/482* (2013.01); *G01T 1/2002* (2013.01); *G01T 1/20182* (2020.05); *G01T 1/20186* (2020.05); *G01T 1/20188* (2020.05)

(58) Field of Classification Search
　　CPC ....... A61B 6/42; A61B 6/4208; A61B 6/4233; A61B 6/4241; A61B 6/4258; A61B 6/4266; A61B 6/4283; A61B 6/482; G01T 1/20; G01T 1/2006; G01T 1/2008; G01T 1/2018; G01T 1/20182; G01T 1/20185; G01T 1/20186; G01T 1/20187; G01T 1/20188
　　USPC ........ 250/370.09, 370.11; 378/62, 98.8, 98.9
　　See application file for complete search history.

(56) References Cited

U.S. PATENT DOCUMENTS

| | | | | |
|---|---|---|---|---|
| 6,973,161 | B2 * | 12/2005 | Ohtsuki | G01N 23/04 |
| | | | | 378/53 |
| 8,835,860 | B2 * | 9/2014 | Wu | G01T 1/20181 |
| | | | | 250/366 |
| 9,031,189 | B2 * | 5/2015 | Mukaide | G01T 1/29 |
| | | | | 378/53 |
| 9,274,235 | B2 * | 3/2016 | Kang | G01T 1/20184 |
| 9,411,057 | B2 * | 8/2016 | Helm | G01T 1/2018 |
| 9,528,948 | B2 | 12/2016 | Lüghausen et al. | |
| 9,720,102 | B1 * | 8/2017 | Page | G01T 1/20 |
| 10,539,688 | B2 * | 1/2020 | Steadman Booker | |
| | | | | G01T 1/20184 |
| 11,156,727 | B2 * | 10/2021 | Shedlock | G01T 1/20186 |
| 11,346,962 | B2 * | 5/2022 | Ullah | G01T 1/2008 |

(Continued)

*Primary Examiner* — Allen C. Ho
(74) *Attorney, Agent, or Firm* — JCIPRNET

(57) ABSTRACT

An electronic device, including a scintillator layer, a sensor, and a filter, is provided. The sensor overlaps the scintillator layer and includes a first sensing unit and a second sensing unit. The filter includes a first filter unit overlapping the first sensing unit and a second filter unit overlapping the second sensing unit, and the first filter unit and the second filter unit have different thicknesses.

20 Claims, 8 Drawing Sheets

1C

(56)        References Cited

U.S. PATENT DOCUMENTS

| 12,072,235 B2 * | 8/2024 | Eilmsteiner | ........... G01T 1/2002 |
| 12,442,941 B2 * | 10/2025 | Zhou | ..................... G01T 1/2002 |

* cited by examiner

14A

14B

ELECTRONIC DEVICE COMPRISING A FILTER, A SCINTILLATOR, A SENSOR, AND A SUBSTRATE

CROSS-REFERENCE TO RELATED APPLICATION

This application claims the priority benefit of U.S. provisional application Ser. No. 63/445,717, filed on Feb. 15, 2023, and Taiwan application serial no. 112137049, filed on Sep. 27, 2023. The entirety of each of the above-mentioned patent applications is hereby incorporated by reference herein and made a part of this specification.

BACKGROUND

Technical Field

The disclosure relates to an electronic device.

Description of Related Art

The conventional X-ray examination of an area with soft and hard tissue (for example, chest) requires continuous irradiation of high-energy X-rays and low-energy X-rays to obtain two images corresponding to different energies. Then, image processing is performed on the two images to obtain a clear image of the area. However, if the area shifts during the two X-ray irradiation periods, there will be abnormalities (for example, image blur) in image processing.

SUMMARY

The disclosure provides an electronic device, which helps obtain a clear image.

In an embodiment of the disclosure, the electronic device includes a scintillator layer, a sensor, and a filter. The sensor overlaps the scintillator layer and includes a first sensing unit and a second sensing unit. The filter includes a first filter unit overlapping the first sensing unit and a second filter unit overlapping the second sensing unit, and the first filter unit and the second filter unit have different thicknesses.

In another embodiment of the disclosure, the electronic device includes a scintillator layer, a sensor, and a filter. The sensor is disposed between the filter and the scintillator layer.

In order for the features and advantages of the disclosure to be more comprehensible, the following specific embodiments are described in detail in conjunction with the drawings.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
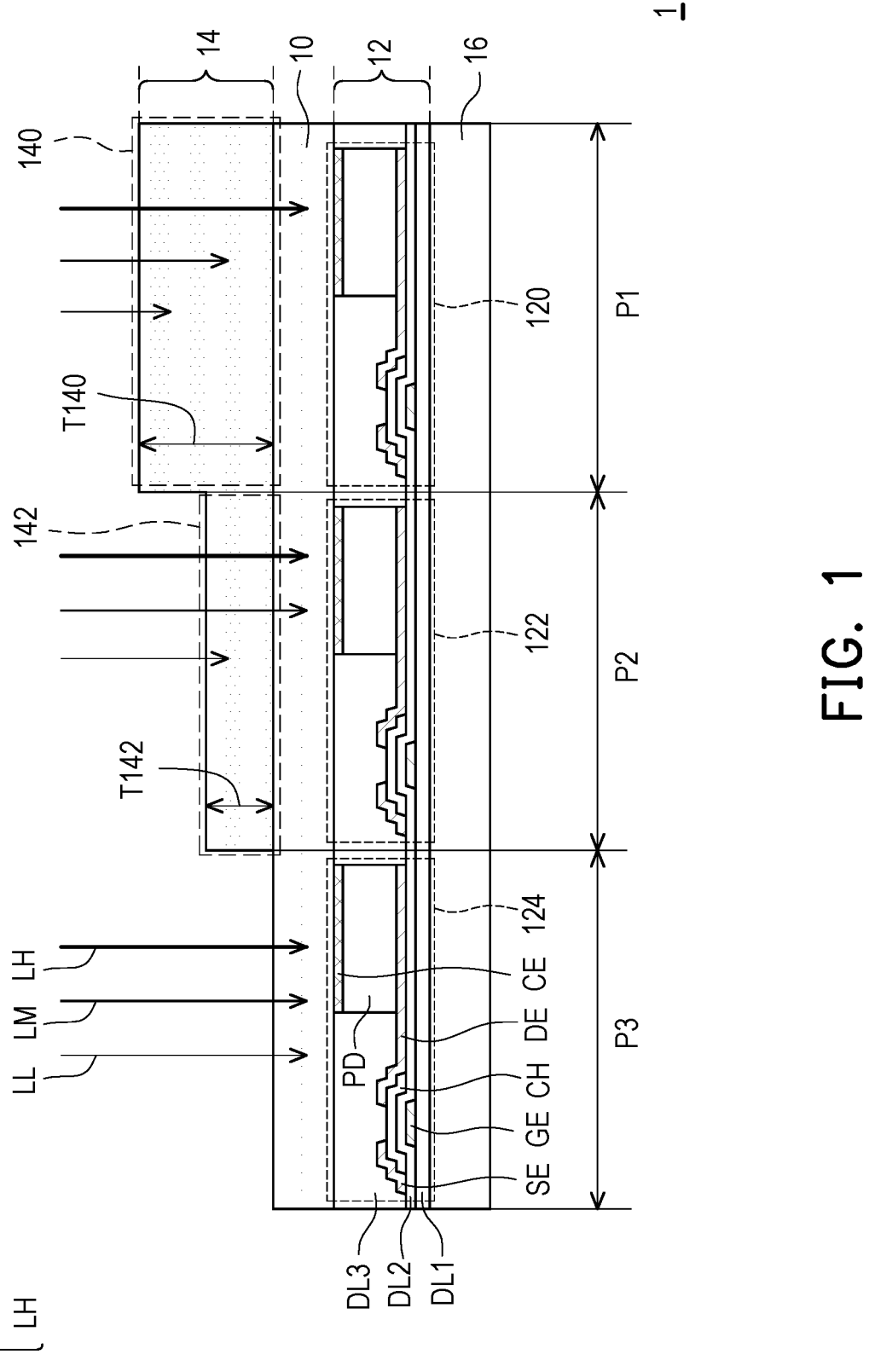
FIG. 1 to FIG. 6 are respectively partial cross-sectional schematic views of various electronic devices according to multiple embodiments of the disclosure.

Reference will now be made in detail to the exemplary embodiments of the disclosure, and examples of the exemplary embodiments are illustrated in the drawings. Wherever possible, the same reference numerals are used in the drawings and the description to refer to the same or similar parts.

Throughout the specification and the appended claims of the disclosure, certain terms may be used to refer to specific elements. It should be understood by persons skilled in the art that electronic device manufacturers may refer to the same element by different names. The disclosure does not intend to distinguish between elements with the same function but different names. In the following specification and claims, words such as "containing" and "comprising" are open-ended words, so the words should be interpreted as "including but not limited to . . . ".

Directional terms such as "upper", "lower", "front", "rear", "left", and "right" mentioned in the disclosure are only directions with reference to the drawings. Therefore, the used directional terms are used to illustrate, but not to limit, the disclosure. In the drawings, each drawing illustrates the general characteristics of a method, a structure, and/or a material used in a specific embodiment. However, the drawings should not be construed to define or limit the scope or nature covered by the embodiments. For example, the relative sizes, thicknesses, and positions of various film layers, regions, and/or structures may be reduced or enlarged for clarity.

When a structure (or layer, element, base) is described in the disclosure as being located on/above another structure (or layer, element, base), it may mean that the two structures are adjacent and directly connected or it may mean that the two structures are adjacent but not directly connected. Indirect connection means that there is at least one intermediate structure (or intermediate layer, intermediate element, intermediate base, intermediate spacing) between the two structures. A lower surface of one structure is adjacent or directly connected to an upper surface of the intermediate structure, and an upper surface of the other structure is adjacent or directly connected to a lower surface of the intermediate structure. The intermediate structure may be composed of a single-layer or multi-layer physical structure or non-physical structure, but not limited thereto. In the disclosure, when a certain structure is disposed "on" another structure, it may mean that the certain structure is "directly" on the other structure or it may mean that the certain structure is "indirectly" on the other structure, that is, at least one structure is also sandwiched between the certain structure and the other structure.

The terms "about", "equal to", "equivalent" or "the same", "substantially", or "approximately" are generally interpreted as within 20% of a given value or range, or interpreted as within 10%, 5%, 3%, 2%, 1%, or 0.5% of the given value or range. In addition, the terms "a range is from a first value to a second value" and "the range is between the first value and the second value" mean that the range includes the first value, the second value, and other values therebetween.

Ordinal numbers such as "first" and "second" used in the specification and the claims are used to modify elements and do not imply and represent that the elements have any previous ordinal numbers, nor do they represent the order of a certain element and another element or the order of a manufacturing method. The use of the ordinal numbers is only used to clearly distinguish between an element with a certain name and another element with the same name. The claims and the specification may not use the same terms, whereby a first component in the specification may be a second component in the claims.

In some embodiments of the disclosure, terms such as "connection" and "interconnection" related to bonding and connection, unless otherwise specified, may mean that two structures are in direct contact, or may also mean that the two structures are not in direct contact, wherein there is another structure between the two structures. Also, the terms related to bonding and connection may also include the case where the two structures are both movable or the two structures are both fixed. In addition, the term "coupling" includes any direct and indirect means of electrical connection. In addition, the term "link" includes a means of signal communication whereby two elements or devices may directly or indirectly receive and/or transmit wireless signals.

Electrical connection or coupling described in the disclosure may refer to direct connection or indirect connection. In the case of direct connection, end points of elements on two circuits are directly connected or connected to each other with a conductor segment, and in the case of indirect connection, there is a switch, a diode, a capacitor, an inductor, a resistor, other suitable elements, or a combination of the above elements between the end points of the elements on the two circuits, but not limited thereto.

In the disclosure, the measurement manner of thickness, length, and width may be by adopting an optical microscope (OM), and the thickness or the width may be obtained by measuring a cross-sectional image in an electron microscope, but not limited thereto. In addition, there may be a certain error in any two values or directions for comparison. In addition, the term "a given range is from a first value to a second value", "the given range falls within a range of the first value to the second value", or "the given range is between the first value and the second value" means that the given range includes the first value, the second value, and other values therebetween. If a first direction is perpendicular to a second direction, an angle between the first direction and the second direction may be between 80 degrees and 100 degrees; and if the first direction is parallel to the second direction, the angle between the first direction and the second direction may be between 0 degrees and 10 degrees.

It should be noted that in the following embodiments, the features in several different embodiments may be replaced, recombined, and mixed to complete other embodiments without departing from the spirit of the disclosure. As long as the features of the embodiments do not violate the spirit of the invention or conflict with each other, the features may be arbitrarily mixed and matched for use.

Unless otherwise defined, all terms (including technical and scientific terms) used herein have the same meaning as commonly understood by persons skilled in the art to which the disclosure belongs. It can be understood that the terms such as the terms defined in commonly used dictionaries should be interpreted as having meanings consistent with the relevant art and the background or context of the disclosure, and should not be interpreted in an idealized or overly formal manner, unless otherwise defined in the embodiments of the disclosure.

The type and the form of an electronic device are not limited. For example, the electronic device may include a display device, a backlight device, an antenna device, a detection device, a splicing device, or any device that requires charging. In addition, the electronic device may be a bendable or flexible electronic device.

The display device may be a non-self-luminous display device or a self-luminous display device. The electronic device may, for example, include liquid crystal, a light emitting diode, fluorescence, phosphor, quantum dot (QD), other suitable display media, or a combination of the above. The antenna device may be a liquid crystal antenna device or a non-liquid crystal antenna device. The detection device may be a detection device for sensing capacitance, light rays (for example, visible light or X-rays), thermal energy, or ultrasonic waves, but not limited thereto. In some embodiments, the electronic device may include an electronic element. The electronic element may include a passive element and an active element, such as a capacitor, a resistor, an inductor, a diode, and a transistor. The diode may include a light emitting diode or a photodiode. The light emitting diode may include, for example, an organic light emitting diode (OLED), a mini LED, a micro LED, or a quantum dot LED, but not limited thereto. The splicing device may be, for example, a display splicing device, a detection splicing device, or an antenna splicing device, but not limited thereto. It should be noted that the electronic device may be any permutation and combination of the above, but not limited thereto. In addition, the shape of the electronic device may be rectangular, circular, polygonal, a shape with curved edges, or other suitable shapes. The electronic device may have a peripheral system such as a driving system, a control system, and a light source system to support the display device, the antenna device, a wearable device (for example, including augmented reality or virtual reality), a vehicle-mounted device (for example, including a car windshield), or the splicing device.

Figure 7:
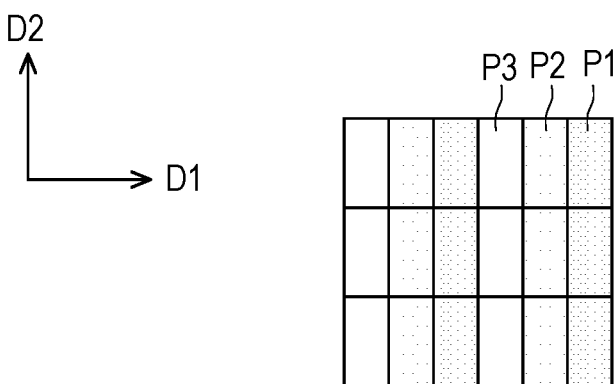
FIG. 7 and FIG. 8 are respectively partial top views of various electronic devices according to multiple embodiments of the disclosure.
Figure 8:
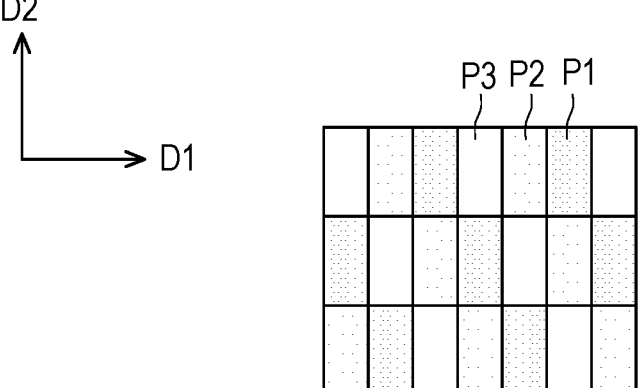
Figure 9:
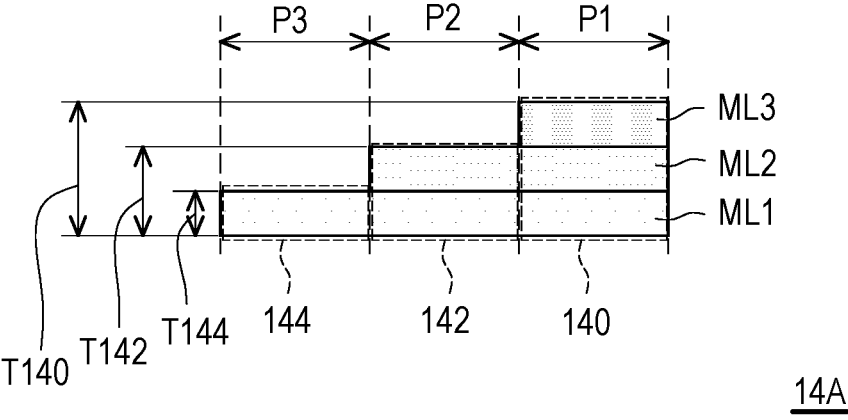
FIG. 9 and FIG. 10 are respectively partial cross-sectional schematic views of various filters according to multiple embodiments of the disclosure.
Figure 10:
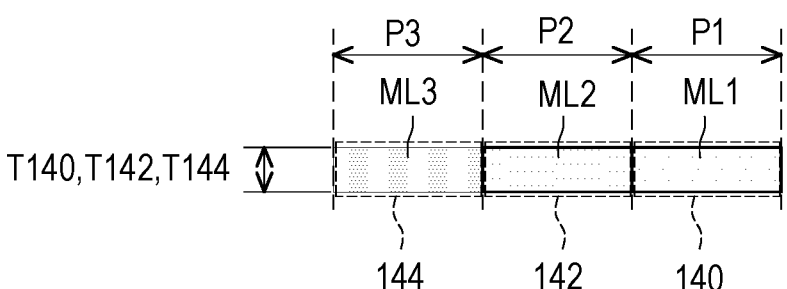

FIG. 1 to FIG. 6 are respectively partial cross-sectional schematic views of various electronic devices according to multiple embodiments of the disclosure. FIG. 7 and FIG. 8 are respectively partial top views of various electronic devices according to multiple embodiments of the disclosure. FIG. 9 and FIG. 10 are respectively partial cross-sectional schematic views of various filters according to multiple embodiments of the disclosure.

Please refer to FIG. 1 first. An electronic device 1 may include a scintillator layer 10, a sensor 12, and a filter 14. The sensor 12 overlaps the scintillator layer 10 and includes a first sensing unit 120 and a second sensing unit 122. The filter 14 includes a first filter unit 140 overlapping the first sensing unit 120 and a second filter unit 142 overlapping the second sensing unit 122, and the first filter unit 140 and the second filter unit 142 have different thicknesses.

The scintillator layer 10 may be used to convert an X-ray L incident on the electronic device 1 into visible light (not shown). The material of the scintillator layer 10 may include cesium iodide (CsI), other types of inorganic scintillator materials, or an organic scintillator material, but not limited thereto. In some embodiments, the scintillator layer 10 may be formed on the sensor 12 through a deposition process. The deposition process may include an evaporation process, but not limited thereto. In other embodiments, although not shown, the scintillator layer 10 may be attached to the sensor 12 through an adhesive layer. The adhesive layer may include optical clear adhesive (OCA) or optical clear resin (OCR), but not limited thereto.

The sensor 12 may be used to sense visible light and generate an image corresponding to the light intensity distribution of the visible light. The sensor 12 may include multiple sensing units arranged in an array to generate a two-dimensional image. FIG. 1 schematically illustrates three sensing units, that is, a first sensing unit 120, a second sensing unit 122, and a third sensing unit 124, but it should be understood that the sensor 12 may include more sensing units.

Each sensing unit may include one or more switch elements and one or more photodetectors electrically connected to the one or more switch elements. The switch element may include, for example, a thin film transistor, an integrated circuit (IC), or other suitable switch elements, but not limited thereto. The photodetector may include, for example, a photodiode, a phototransistor, a metal-semiconductor-metal (MSM) photodetector, or other suitable photodetectors, but not limited thereto.

Taking FIG. 1 as an example, the electronic device 1 may also include a substrate 16 for carrying the sensor 12. The substrate 16 may be a hard substrate, a soft substrate, a curved substrate, a flexible substrate, or any type of substrate. In addition, the light transmittance of the substrate 16 is not limited, that is, the substrate 16 may be a light transmitting substrate, a semi-light transmitting substrate, or a non-light transmitting substrate. For example, the material of the substrate 16 may include glass, sapphire, plastic, ceramic, stainless steel, polyimide (PI), polycarbonate (PC), polyethylene terephthalate (PET), or a combination of the above, but not limited thereto.

The sensor 12 is disposed on the substrate 16 and is located, for example, between the substrate 16 and the scintillator layer 10. The sensor 12 may include a dielectric layer DL1, multiple gates GE, a dielectric layer DL2, multiple semiconductor patterns CH, multiple sources SE, multiple drains DE, multiple photodiodes PD, multiple common electrodes CE, and a dielectric layer DL3, but not limited thereto. According to different requirements, the sensor 12 may add or reduce one or more film layers.

The dielectric layer DL1 is disposed on the substrate 16. The material of the dielectric layer DL1 includes, for example, an organic insulating material, an inorganic insulating material, or a combination of the above. The organic insulating material includes, for example, polymethylmethacrylate (PMMA), epoxy, acrylic-based resin, silicone, polyimide polymer, or a combination of the above, but not limited thereto. The inorganic insulating material includes, for example, silicon oxide or silicon nitride, but not limited thereto.

The gates GE are disposed on the dielectric layer DL1. The materials of the gates GE include, for example, metal or metal stacks, such as aluminum, molybdenum, or titanium/aluminum/titanium, but not limited thereto.

The dielectric layer DL2 is disposed on the dielectric layer DL1 and the gates GE. Reference may be made to the material of the dielectric layer DL1 for the material of the dielectric layer DL2, which will not be repeated here.

The semiconductor patterns CH are disposed on the dielectric layer DL2 and respectively overlap the gates GE. The materials of the semiconductor patterns CH include, for example, silicon semiconductors, oxide semiconductors, or other suitable semiconductor materials. The silicon semiconductor includes, for example, amorphous silicon or polycrystalline silicon. The oxide semiconductor includes, for example, indium tin oxide (ITO), indium zinc oxide (IZO), indium gallium oxide (IGO), or indium gallium zinc oxide (IGZO), but not limited thereto.

The sources SE and the drains DE are disposed on the dielectric layer DL2, and each source SE and the corresponding drain DE are respectively located on two opposite sides of the corresponding semiconductor pattern CH. The materials of the sources SE and the drains DE include, for example, metal or metal stacks, such as aluminum, molybdenum, or titanium/aluminum/titanium, but not limited thereto.

The photodiodes PD are respectively located on the drains DE. The materials of the photodiodes PD include, for example, silicon, germanium, indium gallium arsenide, lead sulfide, or other suitable semiconductor materials.

The common electrodes CE are respectively located on the photodiodes PD. The materials of the common electrodes CE may include transparent conductive materials. The transparent conductive material includes, for example, metal oxide, graphene, other suitable transparent conductive materials, or a combination of the above, but not limited thereto. The metal oxide includes, for example, indium tin oxide, indium zinc oxide, aluminum tin oxide, aluminum zinc oxide, indium germanium zinc oxide, or other metal oxides.

The dielectric layer DL3 is disposed on the dielectric layer DL2, the semiconductor patterns CH, the sources SE, and the drains DE. Reference may be made to the material of the dielectric layer DL1 for the material of the dielectric layer DL3, which will not be repeated here.

In FIG. 1, each sensing unit includes, for example, a switch element and a photodetector, wherein the switch element includes one gate GE, one semiconductor pattern CH, one source SE, and one drain DE, and the photodetector includes one photodiode PD. However, the number of switch elements included in each sensing unit, the number of photodetectors included in each sensing unit, the type of switch elements, or the type of photodetectors may be changed according to requirements and are not limited to what is shown in FIG. 1.

The filter 14 may be disposed on the scintillator layer 10, and the scintillator layer 10 may be disposed between the filter 14 and the sensor 12, but not limited thereto. The filter 14 may be used to filter X-rays. In some embodiments, the filter 14 may adopt a pixel design. For example, the filter 14 has different materials and/or thicknesses in different pixels (for example, pixel P1, pixel P2, and pixel P3) to filter X-rays with different energies (for example, low-energy X-ray LL, medium-energy X-ray LM, and high-energy X-ray LH), so that the scintillator layer 10 in different pixels receives the X-rays with different energies and excites visible light with different energies, and therefore the sensing unit in different pixels receives the visible light with different energies. In this way, images corresponding to different X-ray energies are obtained under a single X-ray irradiation.

Taking FIG. 1 as an example, the filter 14, for example, covers the pixel P1 and the pixel P2 and exposes the pixel P3, wherein the first filter unit 140 and the second filter unit 142 of the filter 14 respectively overlap the first sensing unit 120 and the second sensing unit 122 and respectively cover the pixel P1 and the pixel P2. The first filter unit 140 and the second filter unit 142 may have different thicknesses or materials. In some embodiments, a thickness T140 of the first filter unit 140 is, for example, greater than a thickness T142 of the second filter unit 142. In some embodiments, the first filter unit 140 and the second filter unit 142 may include the same materials. In other embodiments, the first filter unit 140 and the second filter unit 142 may include different materials. For example, the materials of the first filter unit 140 and the second filter unit 142 include lead (Pb), copper (Cu), molybdenum (Mo), tungsten (W), rhodium (Rh), aluminum (Al), or other materials suitable for shielding X-rays.

In addition, the filter 14 may be formed through 3D printing, lathe processing, chemical etching, lamination, or a combination of the above. It should be understood that the material of a conductive layer in the sensor 12 may include the same material as the first filter unit 140 and the second filter unit 142. However, since the thickness of the conductive layer in the sensor 12 is very thin relative to the filter 14, the conductive layer may be regarded as transmittable to X-rays.

In the case where multiple filter units have the same material and different thicknesses, the energies of X-rays must be stronger to pass through thicker filter units and be transmitted to the scintillator layer 10 below the filter 14. In FIG. 1, the first filter unit 140 filters out, for example, the low-energy X-ray LL and the medium-energy X-ray LM, so that only the high-energy X-ray LH can irradiate the scintillator layer 10 in the pixel P1. On the other hand, the second filter unit 142 filters out, for example, the low-energy X-ray LL, so that the medium-energy X-ray LM and the high-energy X-ray LH can irradiate the scintillator layer 10 in the pixel P2. In addition, since the pixel P3 is not covered by the filter 14, the scintillator layer 10 in the pixel P3 may receive the low-energy X-ray LL, the medium-energy X-ray LM, and the high-energy X-ray LH.

The X-rays with different energies are separated through a pixelized filter, so as to obtain the images corresponding to different X-ray energies under a single X-ray irradiation. Since it is not necessary to obtain the images corresponding to different X-ray energies through multiple X-ray irradiations, abnormalities in image processing caused by an area shifting during multiple X-ray irradiation periods can be improved, and a clear image can be obtained.

Although FIG. 1 schematically illustrates the pixelized design of the filter using three pixels as filter modulation units, the disclosure is not limited thereto. In other embodiments, two pixels or more than four pixels may be used as the filter modulation units. In addition, the pixelized design is not limited to the filter exposing some pixels and covering the remaining pixels. In other embodiments, although not shown, the filter may cover all pixels, wherein the filter units in different pixels may have the same material and different thicknesses, the filter units in different pixels may have different materials and the same thickness, or the filter units in different pixels may have different materials and different thicknesses. In other words, different filter units may have different thicknesses or materials. The following embodiments may all be modified according to the description in this paragraph, which will not be repeated below.

Figure 2:
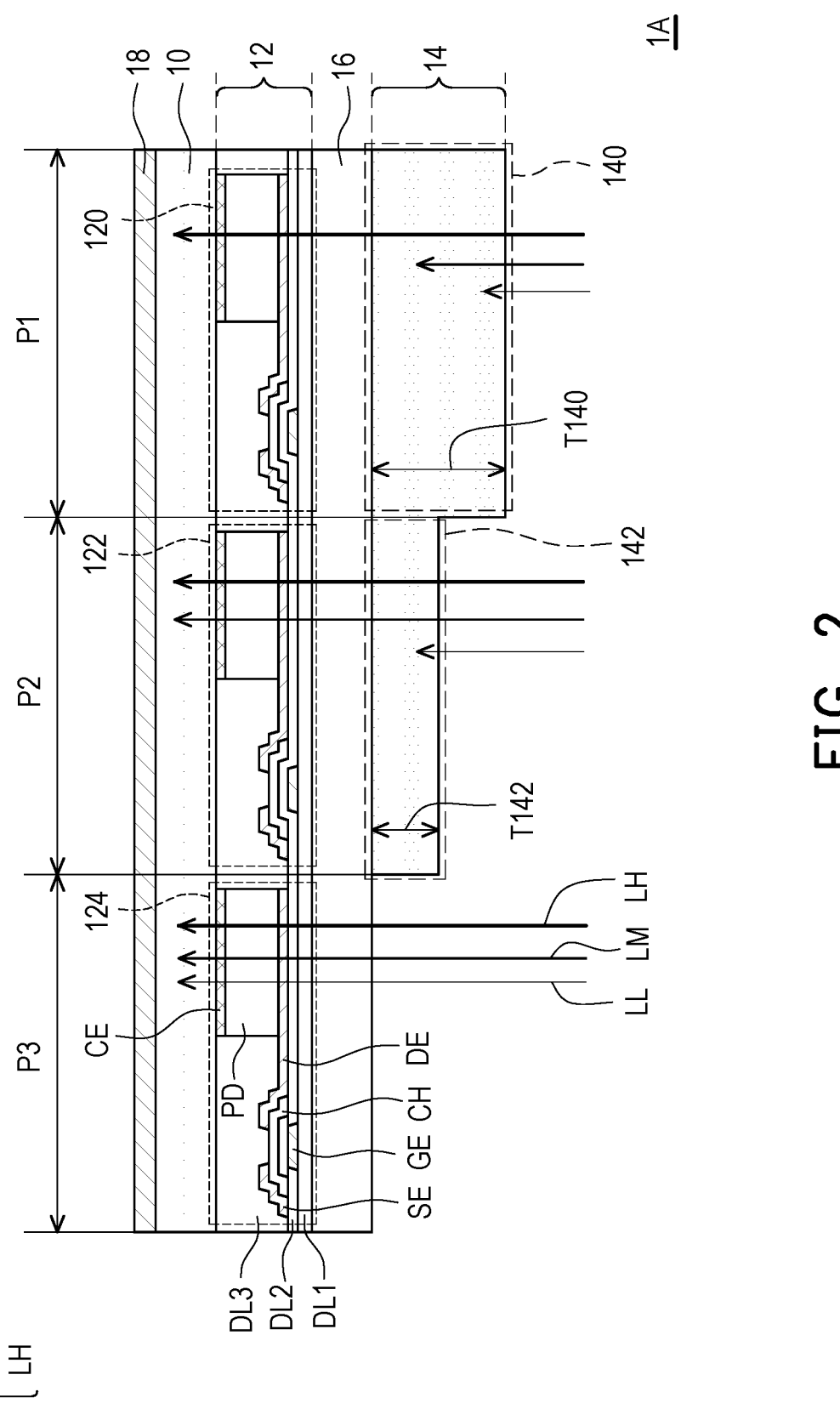

Please refer to FIG. 2. The main difference between an electronic device 1A and the electronic device 1 of FIG. 1 is explained below. In the electronic device 1A, the sensor 12 is disposed between the filter 14 and the scintillator layer 10. For example, the sensor 12 and the filter 14 may be respectively disposed on two opposite surfaces of the substrate 16, and the sensor 12 may be disposed between the scintillator layer 10 and the substrate 16. Through the above design, the path length of visible light to the photodetector (for example, the photodiode PD) can be reduced, which helps to increase the intensity of the visible light received by the sensor 12, so that the image is clearer.

In some embodiments, the electronic device 1A may also optionally include a reflection layer 18. The reflection layer 18 is disposed on a surface of the scintillator layer 10 away from the sensor 12 to reflect the visible light transmitted away from the sensor 12, which helps to increase the intensity of the visible light received by the sensor 12, so that the image is clearer.

Figure 3:
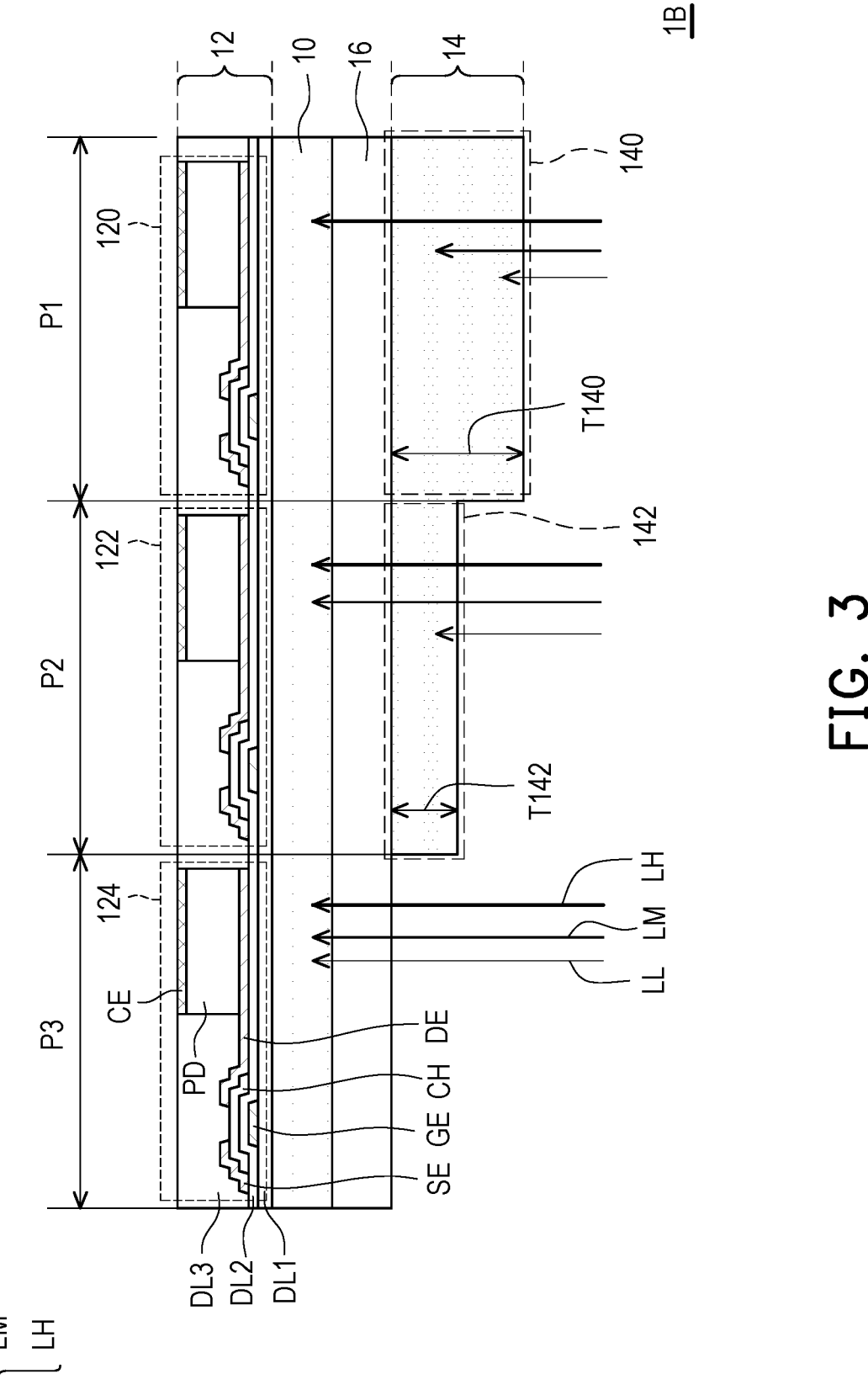

Please refer to FIG. 3. The main difference between an electronic device 1B and the electronic device 1A of FIG. 2 is explained below. In the electronic device 1B, the scintillator layer 10 is disposed between the sensor 12 and the substrate 16. In addition, the electronic device 1B, for example, omits the reflection layer 18 in FIG. 2.

Figure 4:
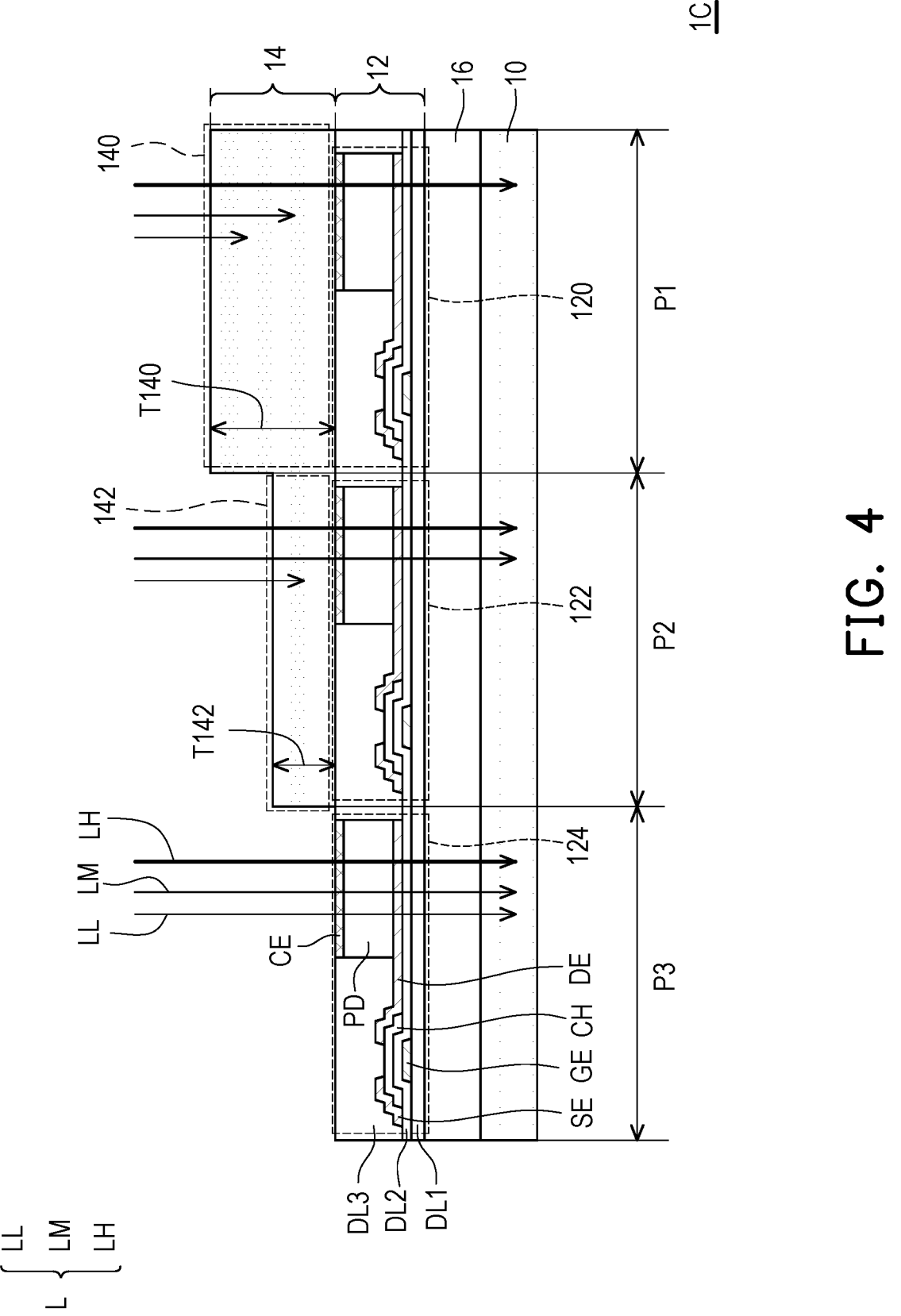

Please refer to FIG. 4. The main difference between an electronic device 1C and the electronic device 1 of FIG. 1 is explained below. In the electronic device 1C, the scintillator layer 10 and the sensor 12 are respectively disposed on the two opposite surfaces of the substrate 16. In addition, the electronic device 1B, for example, omits the reflection layer 18 in FIG. 2.

In some embodiments, although not shown, the electronic device 1C may also include a reflection layer, and the reflection layer is disposed on the surface of the scintillator layer 10 away from the sensor 12 to increase the intensity of the visible light received by the sensor 12, so that the image is clearer.

Figure 5:
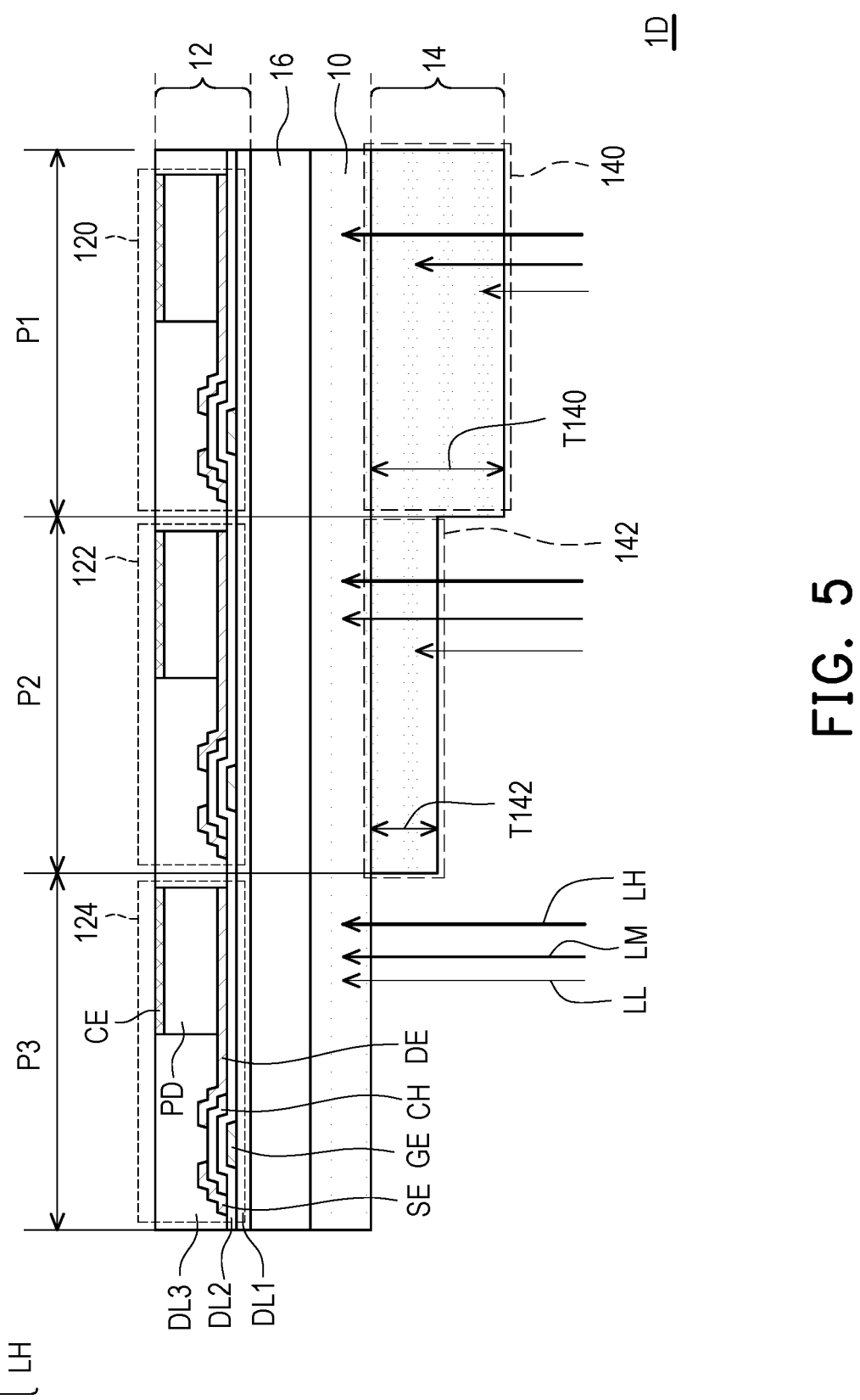

Please refer to FIG. 5. The main difference between an electronic device 1D and the electronic device 1B of FIG. 3 is explained below. In the electronic device 1D, the scintillator layer 10 is disposed between the substrate 16 and the filter 14.

Figure 6:
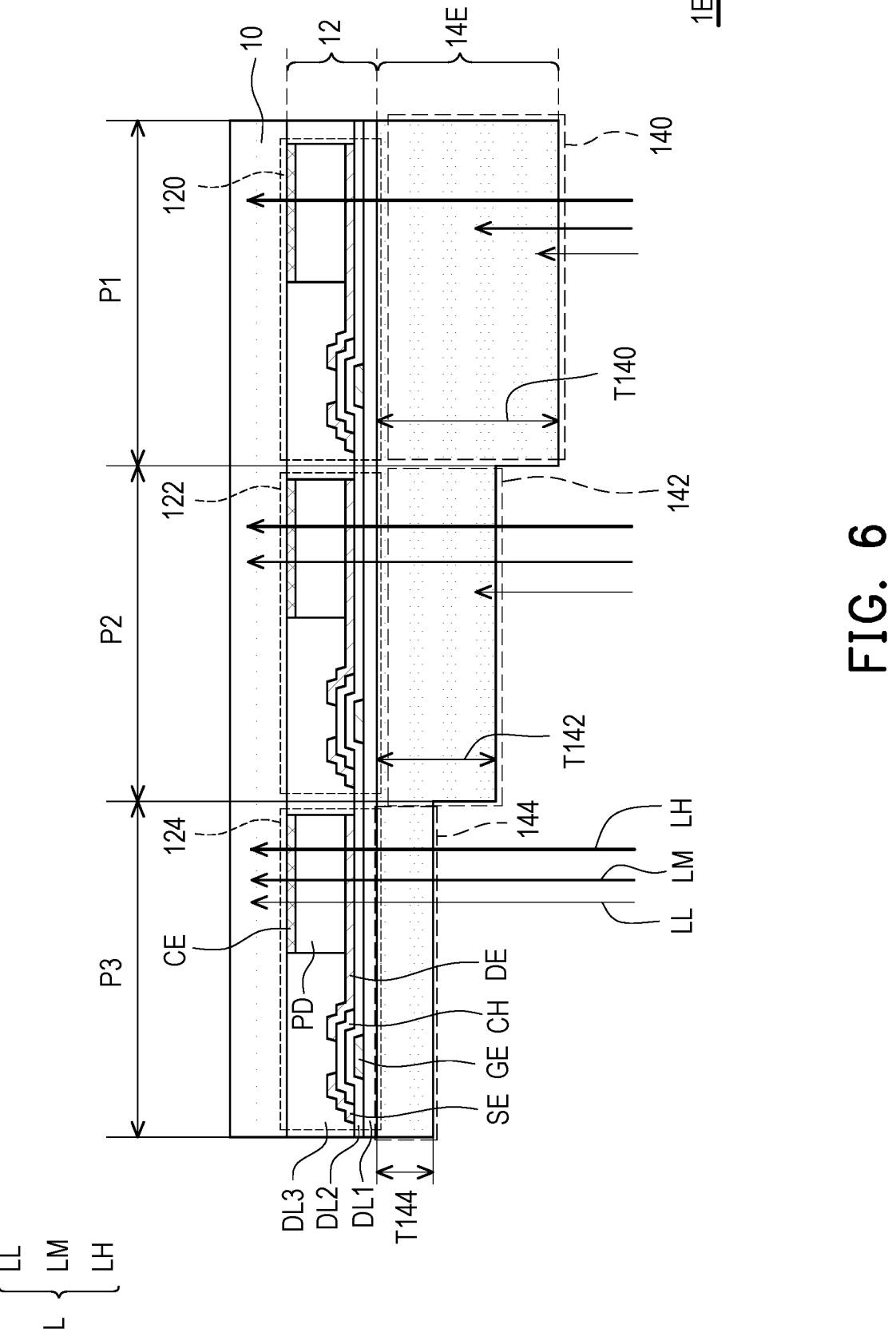

Please refer to FIG. 6. The main difference between an electronic device 1E and the electronic device 1A of FIG. 2 is explained below. In the electronic device 1E, a filter 14E is a plate made of a single material with different thicknesses and is used to carry the sensor 12 and the scintillator layer 10. For example, the filter 14E has the first filter unit 140, the second filter unit 142, and a third filter unit 144 respectively corresponding to the first sensing unit 120, the second sensing unit 122, and the third sensing unit 124, wherein the thickness T140 of the first filter unit 140 is, for example, greater than the thickness T142 of the second filter unit 142, and the thickness T142 of the second filter unit 142 is, for example, greater than a thickness T144 of the third filter unit 144. In this way, the electronic device 1E may omit the substrate 16 of FIG. 2.

In some embodiments, although not shown, the electronic device 1E may also include a reflection layer, and the reflection layer is disposed on the surface of the scintillator layer 10 away from the sensor 12 to increase the intensity of the visible light received by the sensor 12, so that the image is clearer.

In some embodiments, as shown in FIG. 7, any of the above electronic devices may include multiple pixels P1, multiple pixels P2, and multiple pixels P3. The pixels P1, the pixels P2, and the pixels P3 may be alternately arranged in a direction D1, and the pixels P1, the pixels P2, or the pixels P3 may be arranged in a direction D2. In other embodiments, as shown in FIG. 8, any of the above electronic devices may include multiple pixels P1, multiple pixels P2, and multiple pixels P3. The pixels P1, the pixels P2, and the pixels P3 may be alternately arranged in the direction D1 and the direction D2. It should be understood that the arrangement manner of the pixels P1, the pixels P2, and the pixels P3 may be according to actual requirements and is not limited to what is shown in FIG. 7 and FIG. 8.

In addition, the composition of the filter in the disclosure may also be changed according to actual requirements and is not limited to the above. In some embodiments, as shown in FIG. 9, a filter 14A may include a first material layer ML1, a second material layer ML2, and a third material layer ML3, wherein the first material layer ML1 is disposed in the pixel P1, the pixel P2, and the pixel P3, the second material layer ML2 is disposed in the pixel P1 and the pixel P2 and is not disposed in the pixel P3, and the third material layer ML3 is disposed in the pixel P1 and is not disposed in the pixel P2 and the pixel P3. In other words, the first filter unit 140 is composed of the first material layer ML1, the second material layer ML2, and the third material layer ML3, the second filter unit 142 is composed of the first material layer ML1 and the second material layer ML2, and the third filter unit 144 is composed of the first material layer ML1. The materials of the first material layer ML1, the second material layer ML2, and the third material layer ML3 are different and may be selected from lead (Pb), copper (Cu), molybdenum (Mo), tungsten (W), rhodium (Rh), aluminum (Al), or other materials suitable for shielding X-rays. In addition, the thickness T140 of the first filter unit 140 is, for example, greater than the thickness T142 of the second filter unit 142, and the thickness T142 of the second filter unit 142 is, for example, greater than the thickness T144 of the third filter unit 144.

In other embodiments, as shown in FIG. 10, a filter 14B may include the first material layer ML1, the second material layer ML2, and the third material layer ML3, wherein the first material layer ML1 is disposed in the pixel P1 and is not disposed in the pixel P2 and the pixel P3, the second material layer ML2 is disposed in the pixel P2 and is not disposed in the pixel P1 and the pixel P3, and the third material layer ML3 is disposed in the pixel P3 and is not disposed in the pixel P1 and the pixel P2. In other words, the first filter unit 140 is composed of the first material layer ML1, the second filter unit 142 is composed of the second material layer ML2, and the third filter unit 144 is composed of the third material layer ML3. The materials of the first material layer ML1, the second material layer ML2, and the third material layer ML3 are different and may be selected from lead (Pb), copper (Cu), molybdenum (Mo), tungsten (W), rhodium (Rh), aluminum (Al), or other materials suitable for shielding X-rays. In addition, the thickness T140 of the first filter unit 140 is, for example, equal to the thickness T142 of the second filter unit 142, and the thickness T142 of the second filter unit 142 is, for example, equal to the thickness T144 of the third filter unit 144, but not limited thereto. In other embodiments, although not shown, the thickness T140, the thickness T142, and the thickness T144 may be different.

In summary, in the embodiments of the disclosure, the X-rays with different energies are separated through the pixelized filter, so as to obtain the images corresponding to different X-ray energies under a single X-ray irradiation. Since it is not necessary to obtain the images corresponding to different X-ray energies through multiple X-ray irradiations, the abnormalities in image processing caused by the area shifting during the X-ray irradiation periods can be improved, and the clear image can be obtained.

The above embodiments are only used to illustrate, but not to limit, the technical solutions of the disclosure. Although the disclosure has been described in detail with reference to the above embodiments, persons skilled in the art should understand that the technical solutions described in the above embodiments may still be modified or some or all of the technical features thereof may be equivalently replaced. However, the modifications or replacements do not cause the essence of the corresponding technical solutions to deviate from the scope of the technical solutions of the embodiments of the disclosure.

Although the embodiments and the advantages of the disclosure have been disclosed above, it should be understood that any person skilled in the art may make changes, substitutions, and modifications without departing from the spirit and scope of the disclosure, and the features of the embodiments may be arbitrarily mixed and replaced to form other new embodiments. In addition, the protection scope of the disclosure is not limited to processes, machines, manufactures, material compositions, devices, methods, and steps in the specific embodiments described in the specification. Any person skilled in the art may understand conventional or future-developed processes, machines, manufactures, material compositions, devices, methods, and steps from the content of the disclosure as long as the same may implement substantially the same functions or obtain substantially the same results as the embodiments described herein when used according to the disclosure. Therefore, the protection scope of the disclosure includes the above processes, machines, manufactures, material compositions, devices, methods, and steps. In addition, each claim constitutes a separate embodiment, and the protection scope of the disclosure further includes combinations of the claims and the embodiments. The protection scope of the disclosure should be defined by the appended claims.

What is claimed is:

1. An electronic device, comprising:
   a scintillator layer;
   a sensor, overlapping the scintillator layer and comprising a first sensing unit and a second sensing unit; and
   a filter, comprising a first filter unit overlapping the first sensing unit and a second filter unit overlapping the second sensing unit, wherein the first filter unit and the second filter unit have different thicknesses.

2. The electronic device according to claim 1, wherein the first filter unit and the second filter unit comprise a same material.

3. The electronic device according to claim 1, wherein the first filter unit and the second filter unit comprise different materials.

4. The electronic device according to claim 1, wherein the scintillator layer is disposed between the filter and the sensor.

5. The electronic device according to claim 4, further comprising:
   a substrate, wherein the sensor, the scintillator layer, and the filter are sequentially disposed on a side of the substrate.

6. The electronic device according to claim 4, further comprising:
   a substrate, having a first side and a second side opposite to each other, wherein the scintillator layer and the sensor are sequentially disposed on the first side of the substrate, and the filter is disposed on the second side of the substrate.

7. The electronic device according to claim 4, further comprising:
   a substrate, having a first side and a second side opposite to each other, wherein the sensor is disposed on the first side of the substrate, and the scintillator layer and the filter are sequentially disposed on the second side of the substrate.

8. The electronic device according to claim 1, wherein the sensor is disposed between the filter and the scintillator layer.

9. The electronic device according to claim 8, further comprising:
   a reflection layer, disposed on a surface of the scintillator layer away from the sensor.

10. The electronic device according to claim 8, further comprising:

a substrate, having a first side and a second side opposite
to each other, wherein the sensor and the scintillator
layer are sequentially disposed on the first side of the
substrate, and the filter is disposed on the second side
of the substrate.

11. The electronic device according to claim 8, further
comprising:
a substrate, having a first side and a second side opposite
to each other, wherein the sensor and the filter are
sequentially disposed on the first side of the substrate,
and the scintillator layer is disposed on the second side
of the substrate.

12. The electronic device according to claim 8, wherein
the filter comprises a plate of a single material with different
thicknesses.

13. An electronic device, comprising:
a scintillator layer;
a sensor; and
a filter, wherein the sensor is disposed between the filter
and the scintillator layer.

14. The electronic device according to claim 13, further
comprising:
a reflection layer, disposed on a surface of the scintillator
layer away from the sensor.

15. The electronic device according to claim 13, further
comprising:
a substrate, having a first side and a second side opposite
to each other, wherein the sensor and the scintillator layer are sequentially disposed on the first side of the
substrate, and the filter is disposed on the second side
of the substrate.

16. The electronic device according to claim 13, further
comprising:
a substrate, having a first side and a second side opposite
to each other, wherein the sensor and the filter are
sequentially disposed on the first side of the substrate,
and the scintillator layer is disposed on the second side
of the substrate.

17. The electronic device according to claim 13, wherein
the sensor comprises a first sensing unit and a second
sensing unit, the filter comprises a first filter unit overlapping
the first sensing unit and a second filter unit overlapping the
second sensing unit, and the first filter unit and the second
filter unit have different thicknesses or materials.

18. The electronic device according to claim 17, wherein
the first filter unit and the second filter unit have a same
thickness and different materials.

19. The electronic device according to claim 17, wherein
the first filter unit and the second filter unit have different
thicknesses and a same material.

20. The electronic device according to claim 13, wherein
the filter comprises a plate of a single material with different
thicknesses.

* * * * *